United States Patent [19]

Harjunmaa

[11] Patent Number: 4,758,523
[45] Date of Patent: Jul. 19, 1988

[54] IMMUNOASSAY METHOD FOR REMOVING EXCESS TRACER

[75] Inventor: Hannu Harjunmaa, Espoo, Finland

[73] Assignee: Labsystems Oy, Helsinki, Finland

[21] Appl. No.: 711,770

[22] Filed: Mar. 14, 1985

[30] Foreign Application Priority Data

Mar. 14, 1984 [FI] Finland ................... 841023

[51] Int. Cl.$^4$ ........................... G01N 33/545
[52] U.S. Cl. ................... 436/531; 436/800; 436/805; 436/810; 436/824; 436/826
[58] Field of Search ............... 436/518, 531, 800, 805, 436/810, 824, 826

[56] References Cited

U.S. PATENT DOCUMENTS 4,645,747  2/1987  Cais et al. ................ 436/542
4,656,143  4/1987  Baker et al. .............. 436/531

*Primary Examiner*—Christine M. Nucker
*Attorney, Agent, or Firm*—Hopgood, Calimafde, Kalil, Blaustein & Judlowe

[57] ABSTRACT

Method for carrying out immunoassays, in which method an antibody (or antigen) labeled with a tracer so as to be fluorescent is attached onto an antigen (or antibody, respectively) present at the inside wall of the measurement vessel, a liquid denser than the sample is added to the measurement vessel, which said denser liquid displaces the liquid from underneath, and both the excitation radiation is passed into the sample and the fluorescent radiation is collected to the detector through the wall or the bottom of the measurement vessel.

7 Claims, No Drawings

IMMUNOASSAY METHOD FOR REMOVING EXCESS TRACER

The present invention is concerned with a fluorometric or phosphorimetric immunoassay method in which an antibody or antigen labeled with a fluorescent or phosphorescent tracer is attached to the inside wall of the measurement vessel.

In fluorometric immunoassays (FIA), the antigen or antibody has been adsorbed, e.g., onto cuvettes or microtiter discs made of polystyrene or polyacrylics. This so-called antigen or antibody bound to the solid phase is allowed to react with the antibody or antigen, respectively, present in the sample to be studied and with the antibody or antigen, respectively, labeled with a fluoroescent molecule. The less antibody or antigen there is present in the sample, the more of the labeled substance adheres to the solid phase. When the labeled antibody or anitgen remaining in the liquid phase is separated, and when the quantity of the labeled substance adhering to the solid phase is measured by means of a fluorometer, the concentration of the antibody or antigen in the sample is found out.

In the prior-art methods, any excessive labeled antibody or antigen must be washed off before the fluorometric measurement.

The object of the present invention is to provide a fluorometric solid-phase immunoassay method in which the excess tracer does not have to be removed out of the measurement vessel before the fluorometric measurement.

In the method of accordance with the invention, the antigen or antibody is attached to the wall or bottom of the measurement vessel, and the fluorescent radiation is measured through the wall or bottom. After the reaction of the sample and of the added, labeled antibody or antigen with the antigen or antibody, respectively, of the solid phase has taken place, a liquid denser than sample is added into the measurement vessel, which said denser liquid displaces the sample from underneath, In the method in accordance with the present invention, emptying and washing of the measurement vessel can be omitted. In this way, all the transfers of liquid related to the assay are additions of liquid. This makes the assay more rapid and faciliates its automatization decisively.

When a liquid denser than the sample is added to the sample in the method, the liquid is most appropriately coloured so that it has a strong absorption of light either at the excitation wavelength of the fluorescence or at the emission wavelength, or at both, being thus, e.g., of black colour. In this way, the fluorescence can also be measured straight from below without interference by the excess tracer or by the background radiation. Thus, the method is preferably accomplished so that the solid phase is placed on the bottom of the measurement vessel and that both the excitation light is passed into the measurement vessel and the fluoroescent light is collected to the detector through the bottom of the measurement vessel.

In the method, the liquid and colouring agent added must, of course, be such that they do not have an effect disturbing the measurement on the reaction between the antigen and antibody and that they do not prevent fluorescence of the tracer.

The colouring, if any, must be so strong that the fluorescence of the tracer present in the free liquid of the sample is not seen to a aignificant extent in the measurement channel. If the coloured liquid is mixed with the sample, the absorption coefficient must be very high. If the coloured liquid does not mix with the sample and is heavier than the sample, an absorption factor of an order of 1/mm of sufficient if the thickness of the coloured liquid layer is several millimetres.

Well suitable for a non-miscible liquid denser than water are, e.g., such fluorinated hydrocarbons as are liquid at the room temperature, such as, e.g., trichlorotrifluoroethane (Freon—113) and dibromotetrafluoroethane (Freon—114B2). These can be coloured black, e.g., by means of fine carbon powder (soot).

According to one embodiment, a liquid denser than water is added into the measurement vessel, which said liquid is allowed to solidify before measurement.

Of course, the method can also be applied to a method in which phosphorescence is made use of.

What is claimed is:

1. A method for carrying out immunoassays which comprises:
    a. binding an antibody or antigen to a solid phase on the walls or bottom of a measurement vessel;
    b. reacting the bound antibody or antigen with a liquid sample suspected of containing an antibody or antigen which will react with the bound antibody or antigen;
    c. reacting the bound antibody or antigen with a second antibody or antigen which is labeled with a fluorescent or phosphorescent tracer, said second antibody or antigen being specific for the bound antibody or antigen;
    d. adding to the measurement vessel a liquid which is denser than the liquid sample such that the denser liquid displaces the liquid sample from below;
    e. exciting the labeled antibody or antigen by means of irradiation; and
    f. detecting the fluorescent or phosphorescent radiation emitted.

2. The method of claim 1, wherein both the exitation radiation is passed into the liquid sample and the fluorescent or phosphorescent radiation is detected through the bottom of the measurement vessel.

3. The method of claim 1, wherein the denser liquid has the property of absorption at the wavelength of the exitation radiation.

4. The method of claim 1, wherein the denser liquid has the property of absorption of the wavelength of the emission radiation.

5. The method of claim 1, wherein the denser liquid is colored black.

6. The method of claim 1, wherein the denser liquid has the property of solidifying following addition to the measurement vessel.

7. The method of claim 3, wherein both the exitation radiation is passed into the liquid sample and the fluorescent or phosphorescent radiation is detected through the bottom of the measurement vessel.

* * * * *

UNITED STATES PATENT AND TRADEMARK OFFICE
CERTIFICATE OF CORRECTION

PATENT NO. : 4,758,523
DATED : July 19, 1988
INVENTOR(S) : Hannu Harjunmaa

It is certified that error appears in the above—identified patent and that said Letters Patent is hereby corrected as shown below:

In claim 4, line 53, after "absorbtion" kindly delete "of" and insert therefore —at—.

Signed and Sealed this

Sixth Day of December, 1988

Attest:

DONALD J. QUIGG

Attesting Officer

Commissioner of Patents and Trademarks